(12) United States Patent
Couchman

(10) Patent No.: US 8,373,411 B2
(45) Date of Patent: Feb. 12, 2013

(54) SENSOR SYSTEM FOR AN IN-LINE INSPECTION TOOL

(75) Inventor: Peter Couchman, Newcastle Upon Tyne (GB)

(73) Assignee: PII Limited, Cramlington (GB)

( * ) Notice: Subject to any disclaimer, the term of this patent is extended or adjusted under 35 U.S.C. 154(b) by 810 days.

(21) Appl. No.: 11/722,482

(22) PCT Filed: Dec. 5, 2005

(86) PCT No.: PCT/GB2005/004657
§ 371 (c)(1),
(2), (4) Date: Oct. 23, 2009

(87) PCT Pub. No.: WO2006/067369
PCT Pub. Date: Jun. 29, 2006

(65) Prior Publication Data
US 2010/0060273 A1    Mar. 11, 2010

(30) Foreign Application Priority Data

Dec. 22, 2004 (GB) .................................. 0428127.5

(51) Int. Cl.
*G01N 27/72* (2006.01)
(52) U.S. Cl. ........... 324/220; 324/225; 324/240; 73/623
(58) Field of Classification Search .................. 324/220, 324/225, 240; 73/623, 643
See application file for complete search history.

(56) References Cited

U.S. PATENT DOCUMENTS

| 4,105,972 | A | * | 8/1978 | Smith ........................... 324/220 |
| 4,330,748 | A | | 5/1982 | Holden |
| 5,115,196 | A | * | 5/1992 | Low et al. ...................... 324/220 |
| 5,442,287 | A | * | 8/1995 | Kammann et al. ............. 324/242 |
| 6,640,655 | B1 | * | 11/2003 | Manzak et al. ................ 73/865.8 |
| 6,847,207 | B1 | * | 1/2005 | Veach et al. ................... 324/220 |
| 7,997,139 | B2 | * | 8/2011 | Owens et al. ................... 73/622 |
| 2003/0151402 | A1 | * | 8/2003 | Kindler .................... 324/207.17 |
| 2003/0183022 | A1 | * | 10/2003 | Sapelnikov et al. .......... 73/865.8 |

FOREIGN PATENT DOCUMENTS

| DE | 301770 | 1/1987 |
| JP | 2002062279 | 8/2000 |
| WO | WO-2004/088301 | 10/2004 |

* cited by examiner

*Primary Examiner* — Arleen M Vazquez
(74) *Attorney, Agent, or Firm* — Potomac Patent Group PLLC

(57) ABSTRACT

In an in-line pipe inspection tool, sensors for inspecting the pipe are mounted on sensor blocks moveable relative to the body of the tool. However, when the sensor blocks move radially to conform to different pipe diameters, the circumferential distances between the sensors changes. To ameliorate the effect of this, the sensor blocks have a shape such that one axial edge of each sensor block circumferentially overlaps the opposite edge of an adjacent sensor block. With such an arrangement, when the sensor block are operating at minimum diameter, part of one sensor block will overlap an adjacent block, in the circumferential direction. As the diameter of the pipeline in which the pig is used increases, the degree of overlap will reduce, and may even reduce to zero, but there will still be no overall axial gaps between the sensor blocks. Thus, by suitable shaping of the sensor blocks the tool can be used with a wide range of pipe diameters.

17 Claims, 10 Drawing Sheets

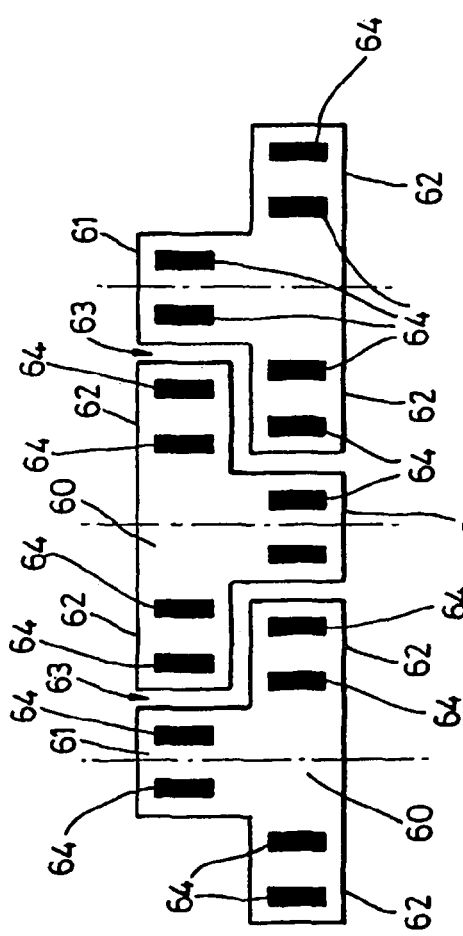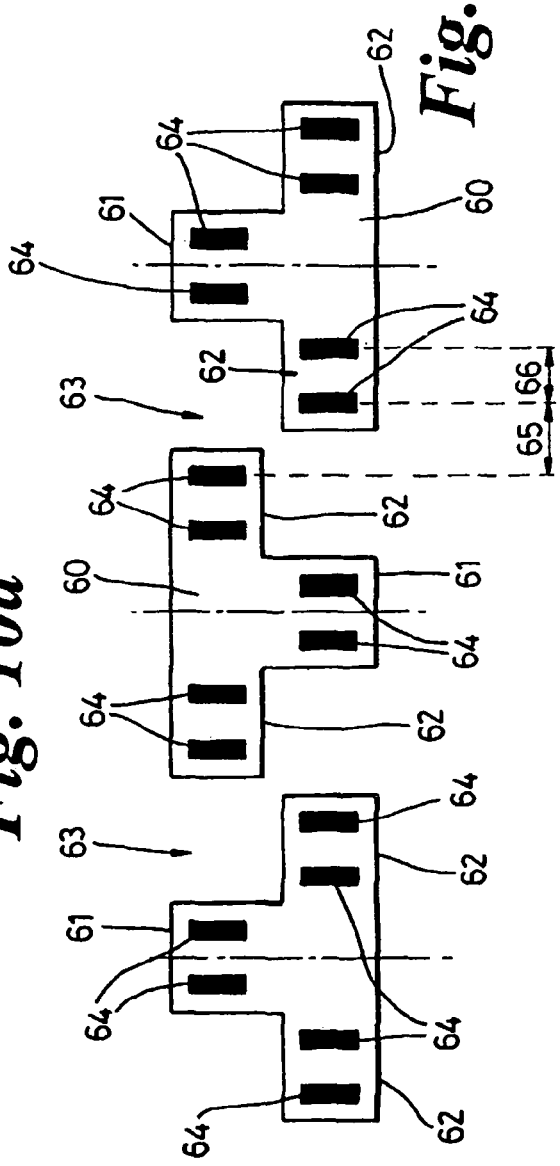
Fig. 10a
Fig. 10b

SENSOR SYSTEM FOR AN IN-LINE INSPECTION TOOL

BACKGROUND OF THE INVENTION

1. Field of the Invention

The present invention relates to a sensor system for an in-line pipe inspection tool. Such an in-line pipe inspection tool is also known as a pipeline pig.

2. Summary of the Prior Art

It is known to inspect a pipeline from the inside using a pipeline pig which passes down the pipe. For magnetic inspection, the pig has permanent magnets defining pole pieces, which are positioned adjacent to the inner wall of the pipe. Those magnets then generate magnetic fields which magnetise the wall of the pipe. Sensors are provided between the magnetic poles, which detect the magnetic flux density at the internal surface of the pipe. The magnetic field in the pipe wall is normally constant, but is disturbed by a flux changing feature, such as a defect, weld bead or wall thickness change, and magnetic flux then leaks out of the pipe at such a feature, to be detected by the sensors. As the pipeline pig is driven along the pipe, the location of the pole pieces, and the sensors, moves along the pipe enabling the internal surface of the pipe to be inspected.

In known arrangements, the sensors may be mounted directly to the body of the pig, but it is more usual to mount them on a sensor carrier, which may also carry the pole pieces of the magnetic pole, and which sensor carrier is connected to the body of the pig by a deformable linkage. Such a deformable linkage permits the sensor carrier to move radially, to allow it to pass e.g. a deformation in the pipe. Thus, the sensor carrier usually forms a body conforming to part of the circumference of a cylinder, and the sensors are mounted on the carrier so as to extend around the circumference of the part-cylinder. Thus, as the pipeline pig moves along the pipeline, the sensors sense an arc of the pipeline, at a given position along the pipeline. Normally, a plurality of such sensor carriers, each with a plurality of sensors, are provided on the pipeline pig, so that the whole circumference of the pipeline can be sensed.

SUMMARY OF THE INVENTION

It is desirable that pipeline pigs may be used in pipelines of a range of diameters, and therefore the sensors are normally mounted in sensor blocks, each of which contains one or a plurality of sensors, and which sensor blocks are themselves mounted on supports, often referred to as fingers, which permit the sensor blocks to move radially relative to the body of the pig. The radial movement of the sensors permit the sensor blocks to conform to pipelines of different diameters, at least over a range of such diameters.

However, where the sensor blocks move radially, it will be appreciated that the circumferential distance between the sensor blocks will then change. The minimum diameter of the pipeline in which the pig can be used then corresponds to that diameter for which the sensor blocks will be in contact with each other, in the circumferential direction. As such a pig is used with larger diameter pipelines, the sensor blocks, and hence the sensors of adjacent blocks, will move apart. This has the problem that the sensing action may be less than optimal for many pipeline diameters for which the pig is intended for use. Attempts have been made to overcome this problem by having more than one sensor block ring, with the sensor rings being axially displaced along the body of the pig. Note that in such arrangements, although we have referred to the sensor blocks being in a ring, they may be in one or more arcs which need not extend all the way around the body.

Therefore, the present invention seeks to provide a sensor arrangement which can adjust to different diameters. At its most general, a first aspect of the present invention proposes that the sensor blocks have a shape such that one axial edge of each sensor block circumferentially overlaps the opposite edge of an adjacent sensor block. That overlapping should occur at least in the radial innermost position of the radial movement of the sensor blocks and possibly may occur over the whole movement range of the sensor blocks. Effectively, any gap between adjacent sensor blocks, at least in the radial innermost position, has ends which are not aligned, so that one axial end of such a gap is displaced circumferentially relative to the other end.

With such an arrangement, when the sensor block are operating at minimum diameter, part of one sensor block will overlap an adjacent block, in the circumferential direction. In such a situation, there is no effective overall circumferential gap between the sensor blocks, when the sensors are viewed as a whole, because although there is a circumferential gap at any axial position, there is no direct axial path between the sensor blocks. As the diameter of the pipeline in which the pig is used increases, the degree of overlap will reduce, and may even reduce to zero, but there will still be no overall axial gaps between the sensor blocks. Indeed, it would still be possible for the sensor blocks to move further apart, and thus have a small overall axial gap, without significant problem.

Thus, a first aspect of the present invention may provide an in-line pipe inspection tool having:

a body;

magnets mounted in said body for generating a magnetic field in a pipe; and a plurality of sensor blocks, each sensor block supporting at least one sensor for sensing said magnetic field;

wherein said sensor blocks are arranged adjacent to each other in an array, the array extending around at least a part of the circumference of the body, each sensor block is movable in a radial direction relative to said body, and each sensor block in the array is shaped such that one axial edge of each sensor block circumferentially overlaps the opposite axial edge of an adjacent sensor block, at least when the sensor blocks are in a radially innermost position.

It should be noted that, in the structure defined above, the terms axial, radial, and circumferential are defined relative to the sensor body, which itself is shaped so as to pass down the pipe, and therefore those terms also normally refer to directions within the pipe, at least when the tool is in use. Moreover, the reference to circumferential overlapping refers to overlapping when viewed in the axial direction. It thus does not require part of one sensor block to overlap another in the radial direction.

As in the known arrangements, each sensor block may support only one sensor, but it is preferable that plurality of the sensors are mounted on each block. It is then possible to mount the sensors so that there is no significant circumferential gap between circumferentially successive sensors, at least over a wide range of possible radial movement of the sensor blocks.

Preferably, each sensor block in the array is shaped that one axial end of each sensor block is circumferentially displaced relative to the other axial end of that sensor. Effectively, the longitudinal axes of the sensor blocks are then inclined relative to the axis of the pig. Then, the circumferential overlapping of adjacent blocks is achieved because the circumferential displacement of the respective axial ends of each sensor means that adjacent sensors have one axial end of one sensor aligned with the opposite axial end of the adjacent sensor.

Preferably an intermediate part of the sensor block is displaced relative to one axial end in the opposite direction from the displacement of the other axial end. Such an arrangement will mean that there will be a circumferential overlap between each sensor block and the sensor blocks on either side. This further assists to minimise the effective axial separation of the sensors.

However, other sensor block arrangements are possible, for example, the sensor blocks may be generally triangular, with alternate sensor blocks having their apexes pointing in opposition axial directions. Note that, with such triangular sensor blocks, the corners of the triangles may be omitted.

Yet a further possibility is that the sensor blocks are "T" shaped with the legs of alternate "T" shaped sensor blocks pointing in opposite axial directions, so that the arms of adjacent "T" shapes overlap in the circumferential direction.

Normally, as in known arrangements, the sensor blocks will be mounted on a carrier via flexible supports, often known as fingers, which allow the sensor blocks to move radially, but maintain their orientation relative to the axis of the pig. For this purpose, the sensor blocks may be mounted on the carrier via sprung or parallelogram linkages. Moreover, as in the known arrangements, the carrier may extend around only a part of the circumference of the pig. It is then possible for there to be multiple sensor arrays, each with its own carrier.

In the first aspect of the invention, discussed above, changes in pipeline diameter are accommodated by radial movement of the sensor blocks. However, the mounting of the sensor blocks on the body, or on a carrier, will limit the amount of radial movement that is possible. It may be necessary for the pig to accommodate large changes in pipeline diameter. Therefore, a second aspect of the invention proposes that sensors are mounted on a carrier, the circumferential length of which is variable. Moreover, it is preferable in such an arrangement that the varying of the circumferential length of the carrier causes a variation in the effective radius of curvature of the carrier. Thus, the carrier itself adapts to different diameters of pipeline, moving the sensors to an appropriate position relative to the pipeline wall.

Whilst this second aspect may be used in conjunction with the first aspect, it can also be used independently.

Thus, the second aspect of the present invention may provide an in-line pipe inspection tool having:
a body;
magnets mounted in said body for generating a magnetic field in a pipe; and
a plurality of sensors for sensing said magnetic field;
wherein said sensors are mounted on sensor blocks, which sensor blocks are arranged adjacent to each other in an array, the array extending around at least a part of the circumference of the body, and the array includes a carrier on which the sensor blocks are mounted, the carrier being of a circumferential length which is variable, thereby to vary the circumferential spacing between the sensor blocks.

There are several different ways of achieving a variation in the carrier circumferential length. For example, it is possible to provide a carrier consisting of the support parts, to which the sensor blocks are connected, with the support parts being themselves interconnected by a deformable link. Then, the support parts may be moved apart, but the deformable link ensures that they maintain appropriate spacing, thereby controlling the spacing of the sensor blocks. Such an arrangement has the advantage that it is also readily possible to vary the effective radius of the carrier. In such an arrangement, the carrier may also comprise plurality of strips which are moveable relative to the other, and act as a backing for the flexible connections. This ensures that the carrier can have sufficient rigidity.

In such an arrangement, the carrier needs to be driven to move circumferentially. One way to achieve this is by having a pig whose body has moveable parts, to adapt to different diameters. As the parts of the body move the carrier is lengthened or shortened.

An embodiment of the present invention will now be described in detail, by way of example, with reference to the accompanying drawings, in which:

FIGS. 10a and 10b show a further sensor block configuration; and

Figure 1:
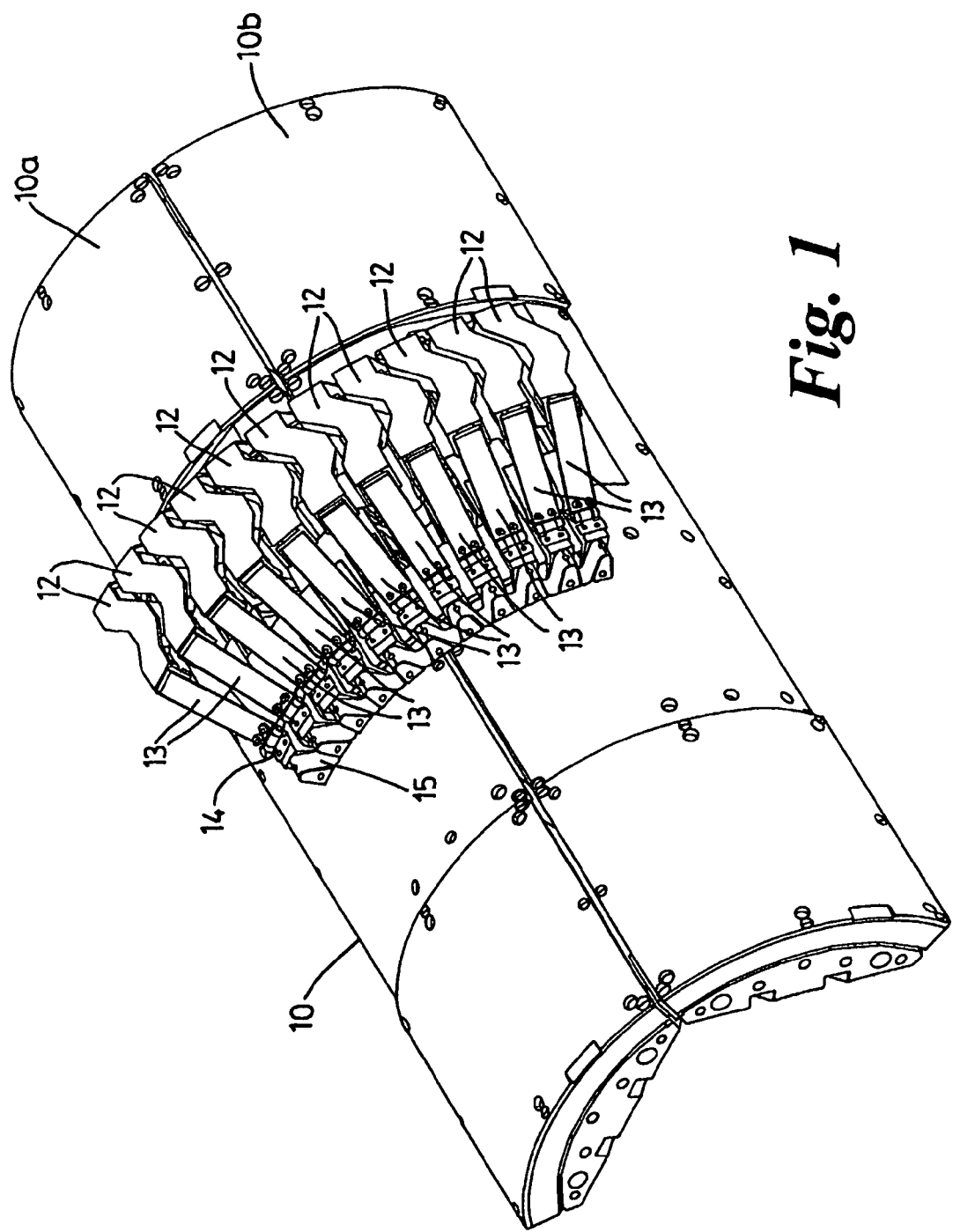
FIG. 1 is a view of part of the body of an in-line pipeline inspection tool, having an array of sensors in accordance with present inventors.

Referring first to FIG. 1, an in-line pipe inspection tool (pipeline pig) has a body 10 with an array of sensor blocks 12 thereon. Each sensor block 12 is connected via a connection 13 to a support 14, which supports are interconnected by a flexible connection 15. Each sensor block 12 is pivotally linked to the connection 13, and each connection 13 is pivotally connected to the corresponding support 14. Thus, the sensor blocks 12 may move radially relative to the body 10 by movement of the connection 13. Moreover, the sensor blocks 12 are able to maintain a fixed orientation relative to the longitudinal axis of the body 10, due to an additional linkage that will be described later.

Figure 2:
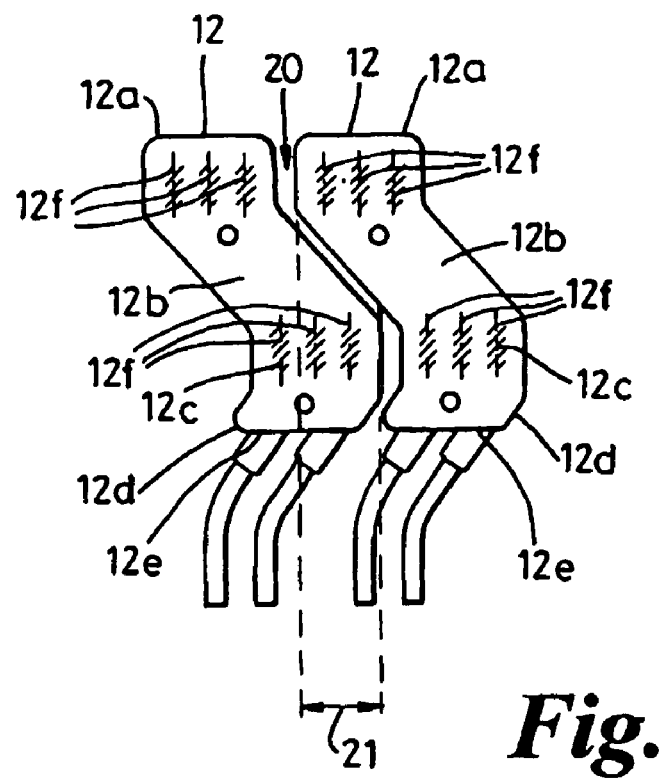
FIG. 2 shows two of the sensors of the embodiment of FIG. 1, in a first position.

FIG. 2 then shows two of the sensor blocks 12 in more detail. It can be seen that each sensor block 12 has a first end 12a at one axial end of the sensor block, which end 12a extends generally perpendicular to the longitudinal axis of the body 10. An intermediate part 12b extends at an angle inclined to the ends 12a, a further intermediate part 12c then extends generally parallel to the longitudinal axis of the body 10, and there is a further inclined part 12d, but inclined in the opposite direction to the part 12b, terminating in an end 12e at the opposite axial end of the sensor 12 from the end 12a. It can been seen that the ends 12e are circumferentially offset relative to the ends 12a, because of the inclination of the parts 12b. This means that the gap 20 between the sensor blocks 12 follows a convoluted path and there is a region 21 in which the sensors 12 overlap in the circumferential direction. Thus, there is no overall gap between the sensor blocks 12, even though there is a gap at any axial position, because there is no direct axial path between the sensor blocks, when in the position shown in FIG. 2.

FIG. 2 also illustrates that each sensor block 12 carries 6 sensors 12*f*, three at each end of the sensor block 12. When the sensor blocks 12 are in the position shown in FIG. 2, the sensors 12*f* at one axial end of one sensor block 12 overlap the sensors 12*f* at the opposite end of the adjacent sensor block 12. In the position shown in FIG. 3, there is no such overlap, but nevertheless the spacing between the end most sensors of adjacent sensor blocks is not significantly greater than the spacing of the sensors 12*f* within a sensor block 12.

Figure 3:
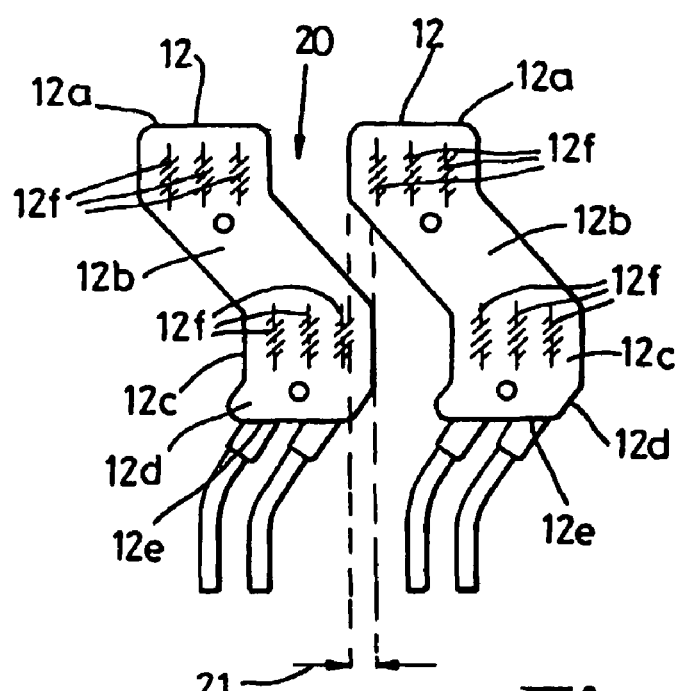
FIG. 3 shows the sensors of FIG. 2, in a second position.

As the sensor blocks 12 move radially outwards, due to pivoting of the links 13, their increased radial separation from the longitudinal axis of the body 10 will mean that they move apart. Thus, as shown in FIG. 3, if the sensor blocks are at an increased radial distance from the longitudinal axis of the body 10, the gap 20 will widen. However, even in the position shown in FIG. 3, there is still an overlap 21 between the sensor blocks 12, although that overlap 21 is reduced as compared with the sensor blocks position shown in FIG. 2. Thus, it would be possible for the sensor blocks to move further apart in the view of FIG. 3, before there was an overall gap between them, i.e. there was no overlap 21. Thus, the use of the sensor blocks 12, which are of convoluted shape, generates the overlap 21 and this improves the performance of the sensors because all parts of the circumference of the pipeline corresponding to the arc of the sensors will be sensed.

Figure 4:
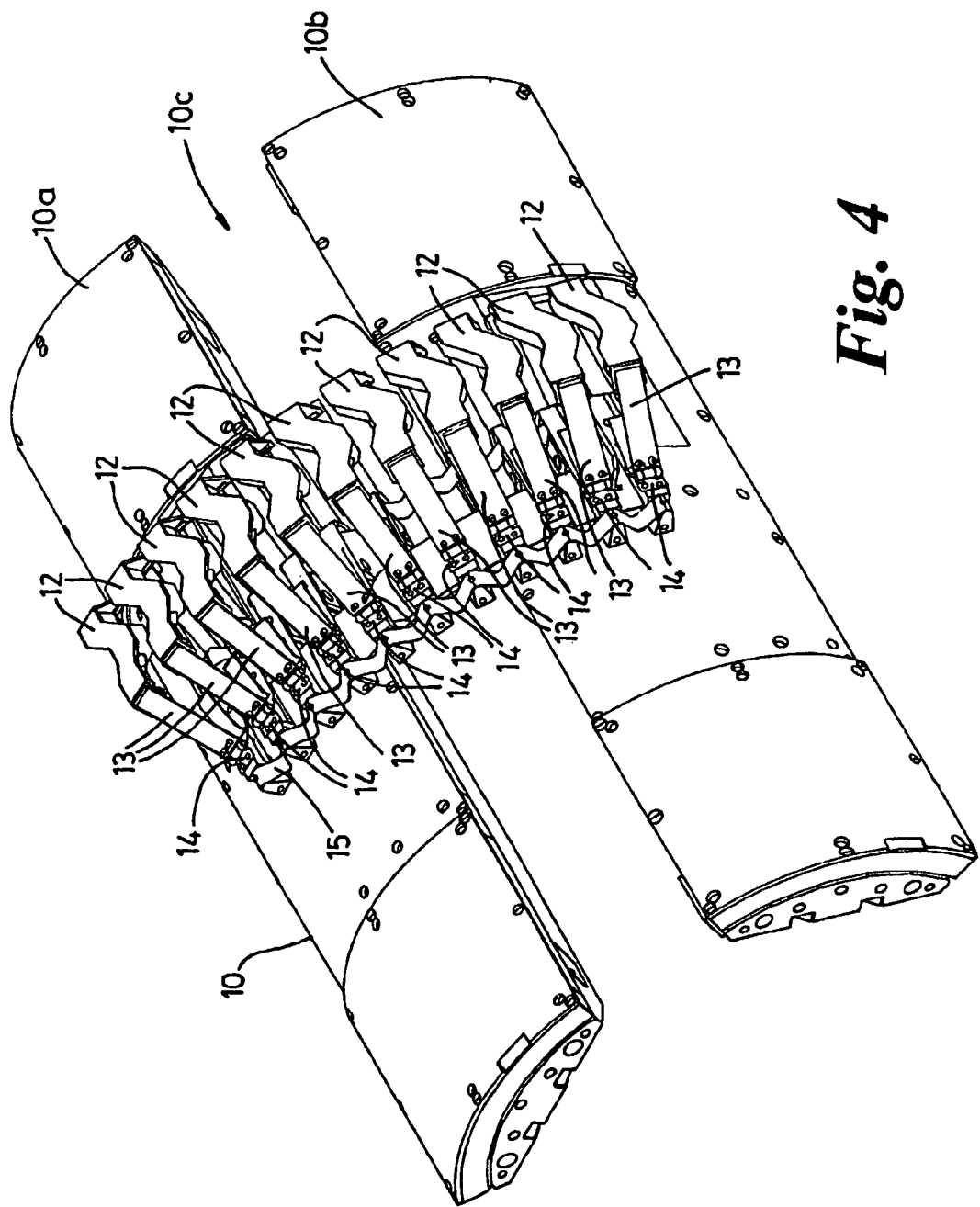
FIG. 4 is a view similar to FIG. 1, but in which the overall circumference of the body has been increased and the circumferential length of the array of sensors increased.

In this embodiment, not only can the sensor blocks 12 move radially, to increase their circumferential separation, but the sensor carrier formed by the supports 14 and the flexible strip 15 is itself of variable circumferential length. In this embodiment, the pig body 10 is deformable, to change its outer diameter. Thus, as illustrated in FIG. 4 two parts 10*a*, 10*b* of the body 10 move radially, to create a gap 10*c*, and in doing so increase the circumference of the body. To compensate for this, the carriers supporting themselves move circumferentially, so that the array of sensors has an increased circumferential length, but the flexible strip 15 deforms by the same amount between each support 14, thereby ensuring that the spacing between the supports 14, and hence the sensor blocks 12, is maintained uniform.

Figure 5:
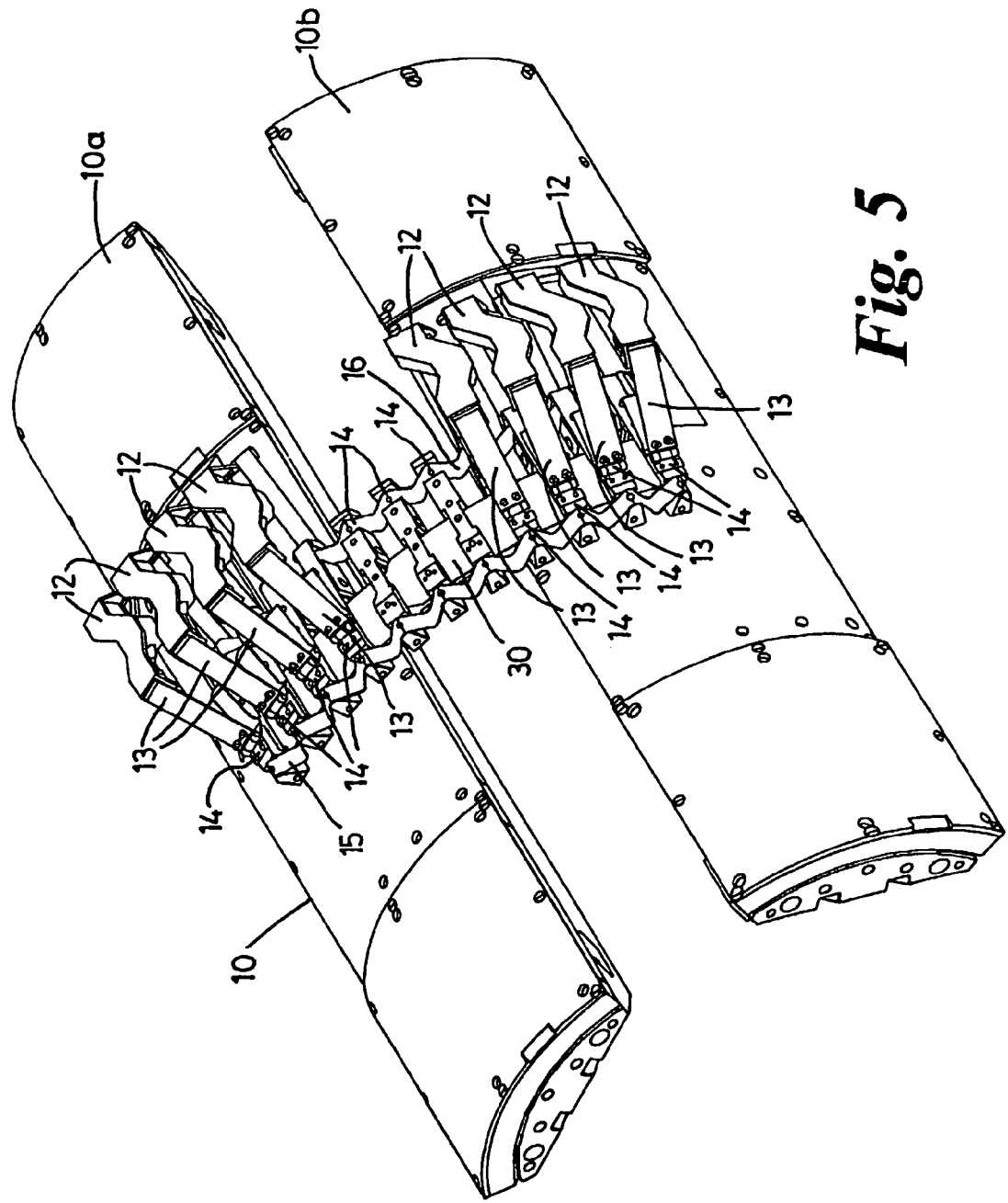
FIG. 5 is a view similar to FIG. 4, but with some of the sensors removed.
Figure 6:
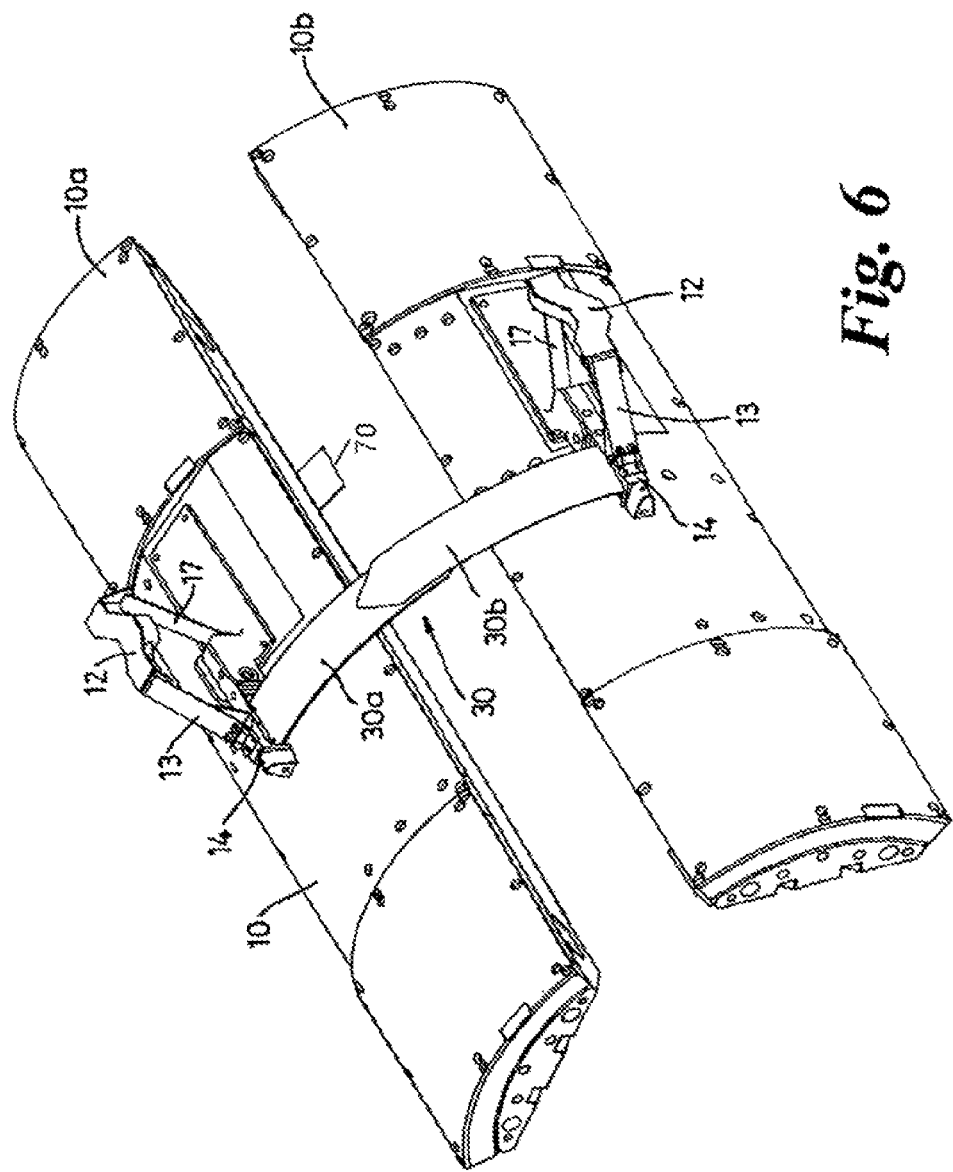
FIG. 6 is a view similar to FIG. 5, but with all but the end sensors, and their associated supports, being removed.

FIG. 5 is a similar view of FIG. 4, but with some of the sensor blocks 12 removed, to enable the supports 14 to be seen more clearly. In particular, FIG. 5 shows that there may be further flexible strip 16 at or adjacent to the opposite ends of the supports 14 from the strip 15, to prevent twisting of the supports 14 relative to the longitudinal axis of the body 10. FIG. 5 also shows that there may be a mounting strip structure 30 linking the supports 14 to provide the support structure for the one of sensor blocks. This strip structure is shown more clearly in FIG. 6, which is a view similar to FIG. 5, but with all but the end sensor blocks 12 of the array removed. It can be seen that the mounting strip structure 30 comprises two overlapping strip parts 30*a*, 30*b* which are fixed to the end supports 14 of the array, and can slip one relative to the other in the circumferential direction. The strip parts 30*a*, 30*b* provide structural support for the arc of sensor blocks. The strips 15, 16 then ensure even circumferential spacing between the supports 14. FIG. 6 also shows a magnet 70 mounted on the body 10.

FIG. 6 also shows that there may be a further flexible linkage 17 between the sensor blocks 12 and the support 14, the purpose of which is to provide, together with the link 13, a parallelogram linkage between the supports 14 and the sensor blocks 12, so that the sensor blocks 12 maintain the correct orientation relative to the longitudinal axis of the body 10. Note that although the linkages 17 are connected between the respective sensor blocks 12 and the supports 14, for the sensor blocks shown in FIG. 6, they will be connected between the sensor blocks 12 and the support 14 for the other sensor blocks, which are omitted from the view of FIG. 6, since those supports 14 will move relative to the body.

Figure 7:
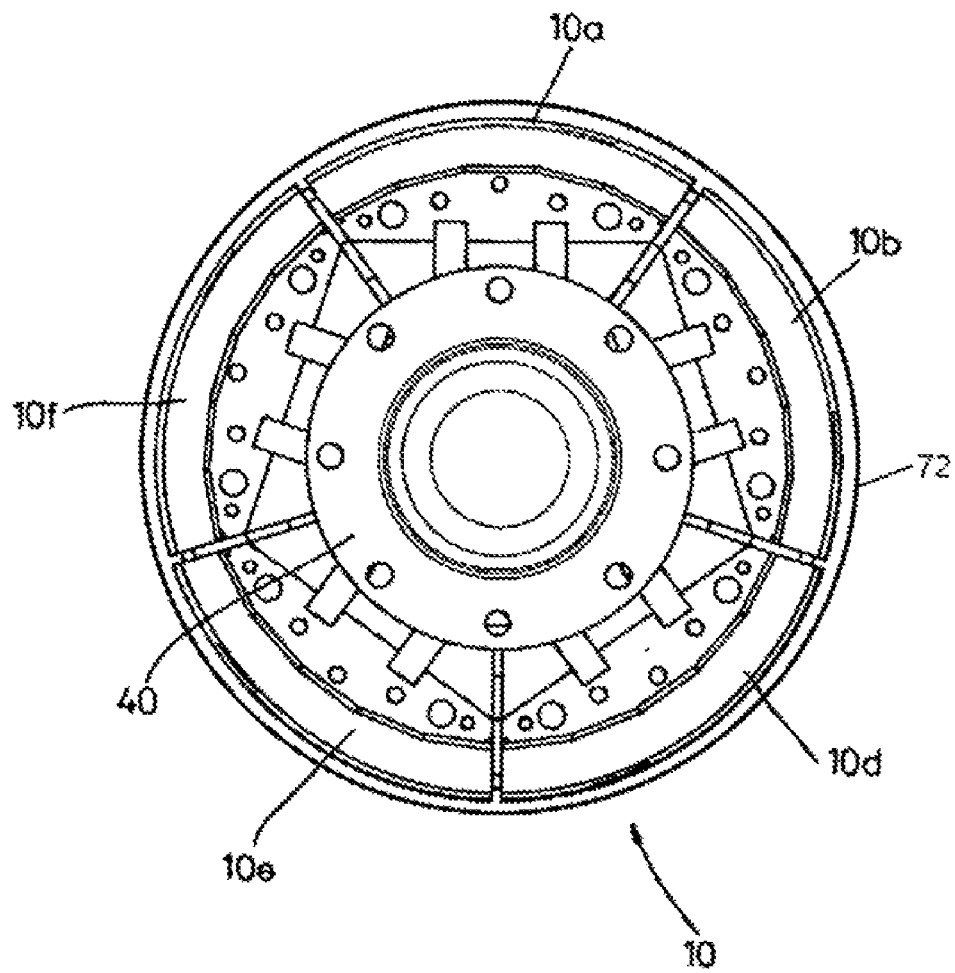
FIG. 7 is an end view of the body of the in-line pipe line inspection tool, as in the position shown in FIG. 1.
Figure 8:
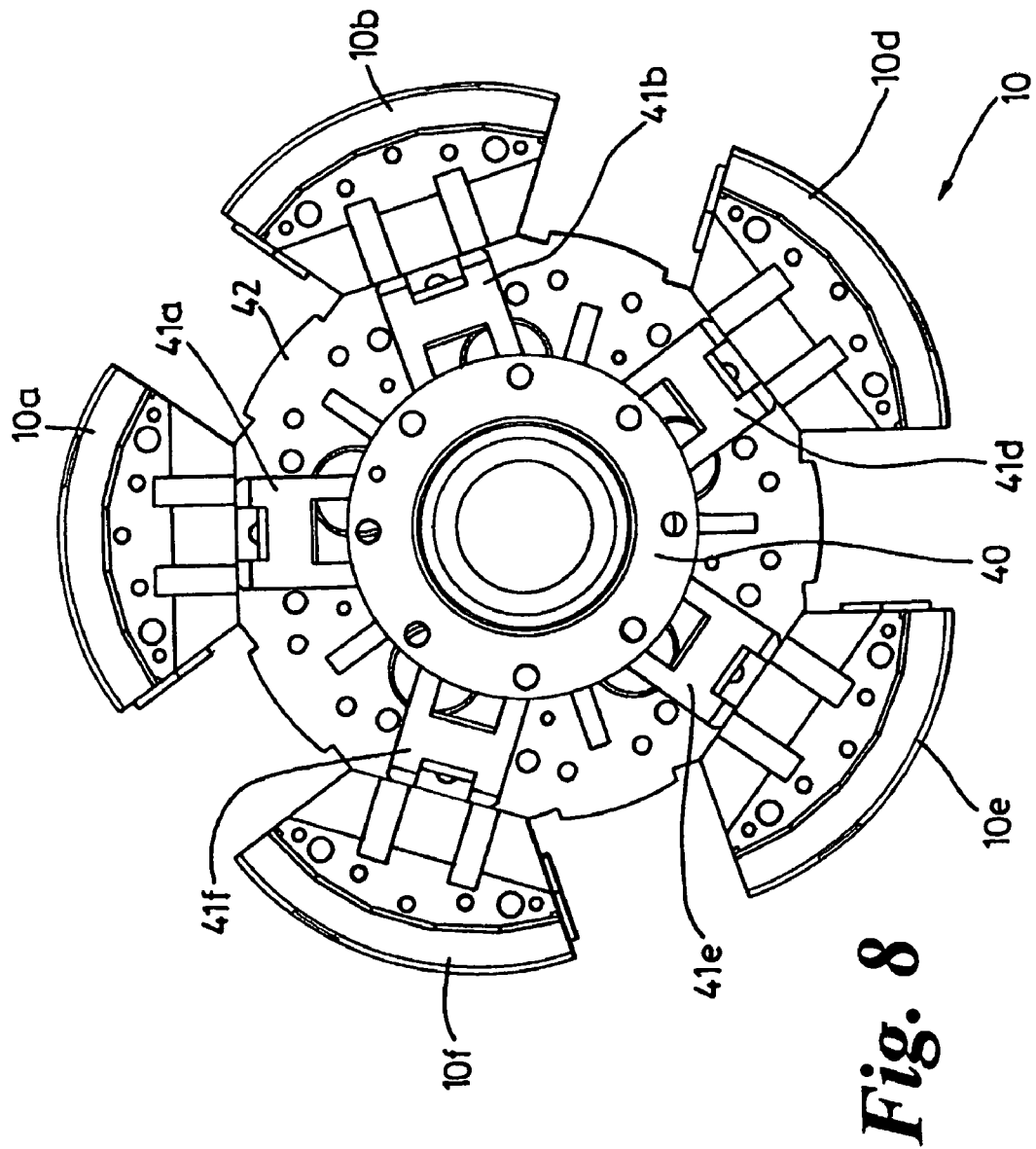
FIG. 8 is an end view of the body, when the overall circumference of the body has been increased as shown in FIG. 4.

As has previously been mentioned, the body 10 has parts which move radially to increase the circumference of the body. This is illustrated in more detail in FIGS. 7 and 8. As shown in FIG. 7, the body 10 may be placed in a pipe 72 and has 5 body parts 10*a*, 10*b*, 10*d*, 10*e* and 10*f*, mounted on a central core 40, with the body parts, 10*a*, 10*b*, 10*d*, 10*e* and 10*f* being movable radially relative to that core 40 to the position shown in FIG. 8. There are then linkages 41*a*, 41*b*, 41*d*, 41*e* and 41*f* between the one 40 and the levelling parts 10*a*, 10*b*, 10*d*, 10*e* and 10*f* to achieve such movement. Note also that the body parts 10*a*, 10*b*, 10*d*, 10*e* and 10*f* of the body 10 need not extend over the full axial length of the body 10, so that there may be another part 42 of the body with no such radial movement.

It is also possible for the body parts 10*a*, 10*b*, 10*d*, 10*e* and 10*f* to move radially by different amounts along their length. The body parts can then adopt a conical shape. However, it is still desirable that the arc of sensor blocks remains uniform and aligned with the wall of the pipe, and this can be achieved as a result of pivots at the mounting points of the sensor block assembly.

It should be noted that the arrangement of the body parts 10*a*, 10*b*, 10*d*, 10*e*, and 10*f* discussed above is described in more detail in U.S. Pat. No. 6,538,431 and will not be discussed in further detail now.

In the arrangements which have been described, the sensor blocks have a convoluted shape in which the first axial end 12*a* is circumferentially offset relative to the opposite axial end 12*e*. However, the present invention is not limited to such a block arrangement. FIGS. 9 to 11 show alternative configurations for the sensor blocks.

Figure 9A:
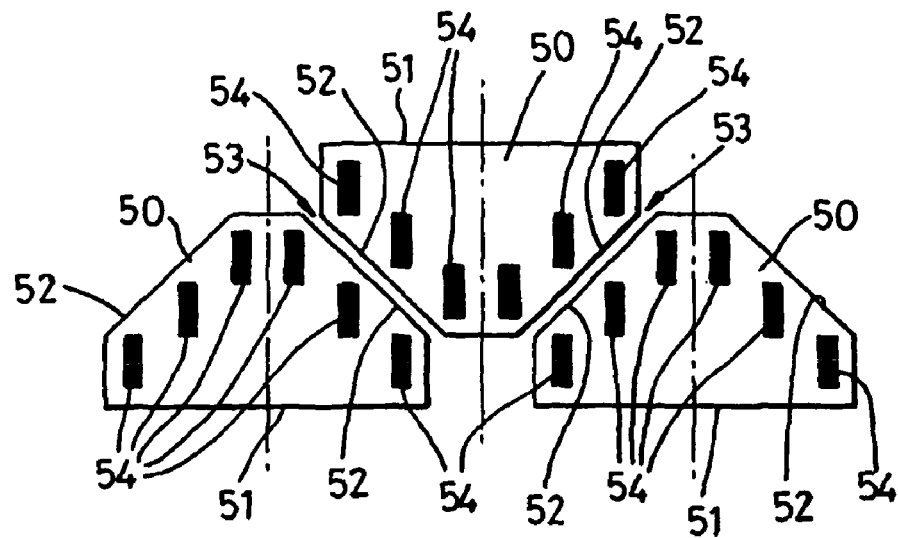
FIGS. 9a and 9b illustrate an alternative sensor block figuration.
Figure 9B:
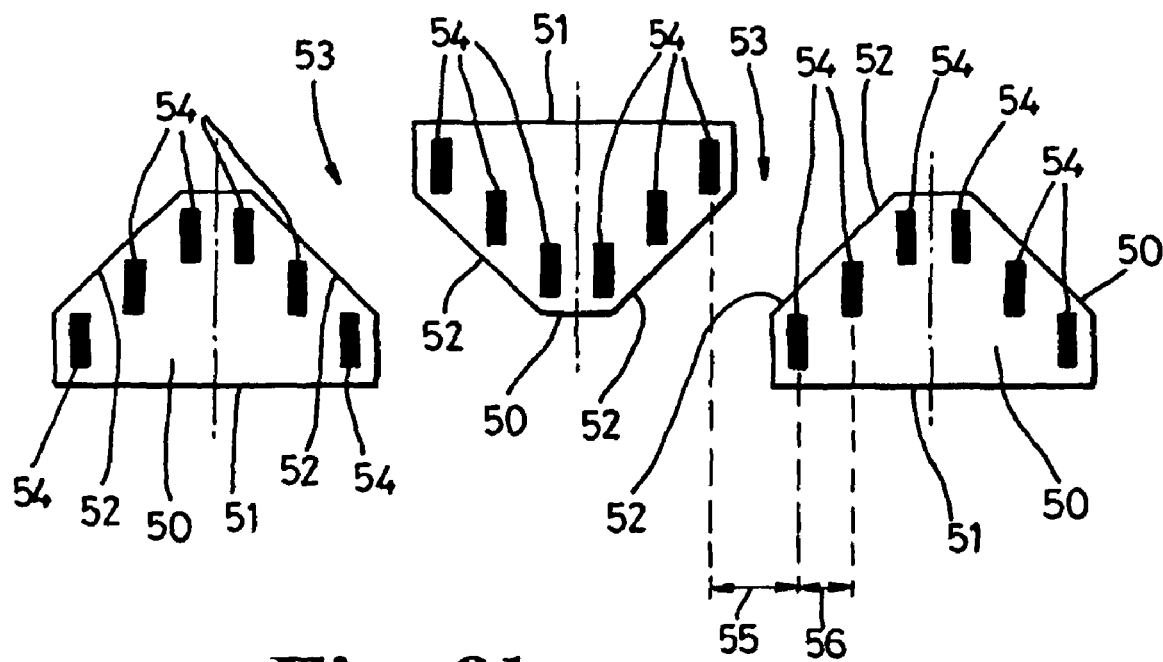

In the arrangement shown in FIGS. 9*a* and 9*b*, the sensor block 50 has a general triangle shape, although the corners of the angles have been removed so they are not needed). Thus, the sensor blocks 50 have an edge 51 which is generally perpendicular to the axis of the body 10, hence to the point, an inclined sides 52. Alternate sensor blocks 50 point in opposite directions, so that the edges 52 of adjacent sensor blocks 50 are parallel. Thus, at the inner most position of the sensor blocks, narrow gaps 53 are defined between adjacent sensor blocks, which gaps 53 are inclined to both the axial and circumferential directions. Moreover, sensors 54 are mounted on the sensor blocks 50, arranged along the inclined edges 52.

Thus, in the innermost position of the sensor blocks 50, shown in FIG. 9*a*, the edge 50 of one sensor block overlaps, in the circumferential direction, the edge 50 of the adjacent sensor block. Thus, in that position, the circumferential spacing of at least one sensor in one block relative to at least one sensor in the adjacent block is not greater than the spacing between the sensors within each block. Thus, sensing can be carried out over the four circumferential extent of the sensor block array. This is true even when the sensor blocks over part to the position shown in FIG. 9*b*. The width of the gaps 53 has increased, and indeed in the position shown in FIG. 9*b* the sensor blocks 50 have moved so that their edges 51 no longer overlap. Nevertheless, the gap 56 between the end most sensors of adjacent sensor blocks is not significantly greater than the gap 56 between adjacent sensors within a block, so that substantially uniform sensing can still be achieved when the sensor blocks 50 are in the position shown in 9*b*, corresponding to the greater remedial position than that shown in FIG. 9*a*.

FIGS. 10*a* and 10*b* illustrate another sensor arrangement, in which the sensor blocks 60 are generally T-shaped, with the legs 61 of adjacent blocks 60 extending in opposite axial direction. Thus, the arms 62 of the sensor block 60 overlap in the circumferential direction, when the sensor blocks 60 are in the inner most radial position. The gap 63 between adjacent sensor blocks is convoluted, with one axial end of each gap 63 being displaced relative to the other axial end.

As shown in FIGS. 10a and 10b, sensors 64 are mounted on the arms 62 and the leg 61 of the sensor block 60. Thus, in the inner most position shown in FIG. 10a, the circumferential spacing between at least one sensor of each adjacent sensor blocks is less than the circumferential spacing of the sensors within each sensor block. Hence, even when the sensor blocks 60 move radially, so increasing their circumferential separation, as shown in FIG. 6b, the circumferential separation 65 between the end most sensor 64 of adjacent sensor blocks 60 is not significantly greater than the spacing 66 between adjacent sensors within the sensor block.

Figure 11A:
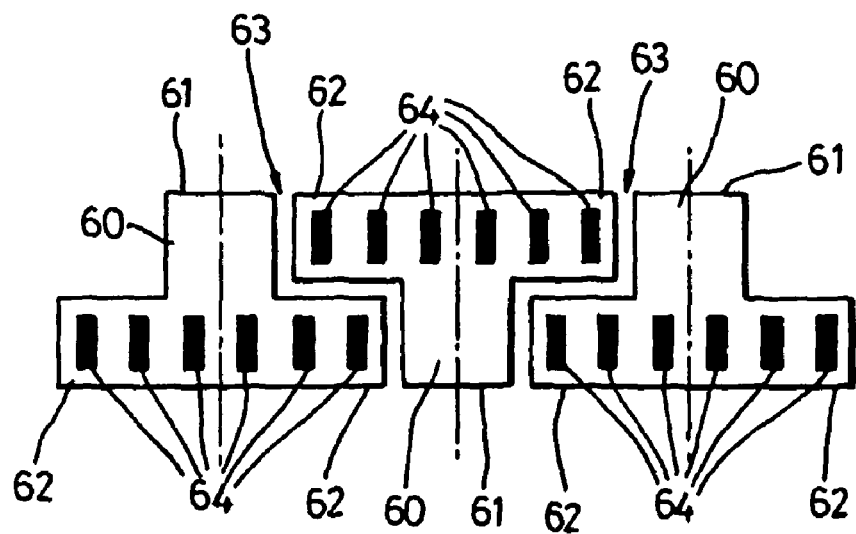
FIGS. 11a and 11b show yet a further sensor block configuration.
Figure 11B:
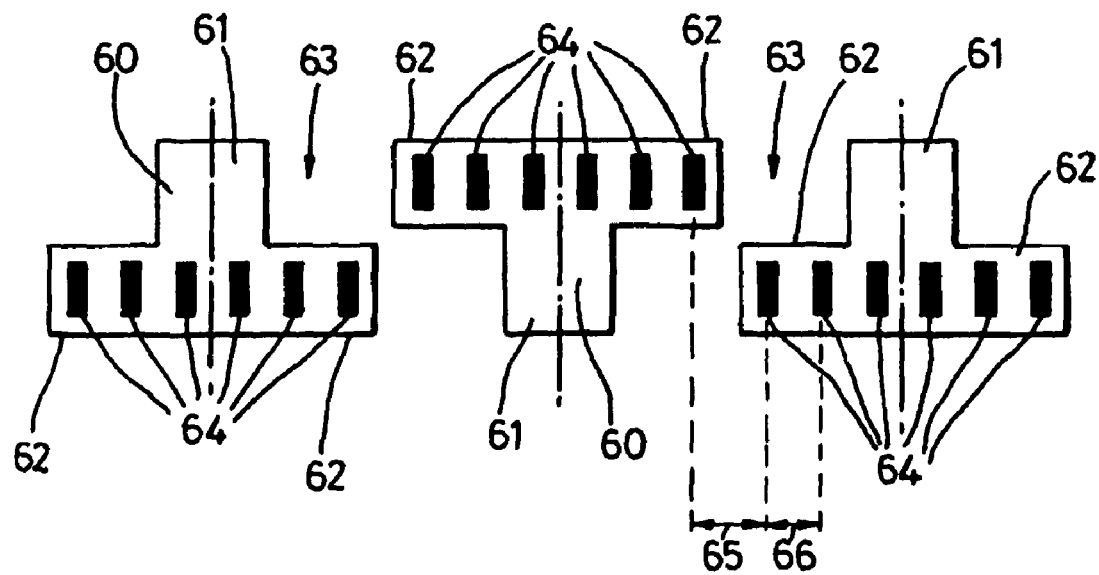

FIGS. 11a and 11b illustrate a modification of the arrangement of FIGS. 10a and 10b, in which the sensors 64 are mounted only on the arms of the "T-shaped" sensor blocks 60. The arrangement of FIGS. 11a and 11b is otherwise the same as that of FIGS. 10a and 10b, and will not be described in further detail. The same reference numerals are used to indicate corresponding parts.

The invention claimed is:

1. An in-line pipe inspection tool having:
a body;
magnets mounted in said body for generating a magnetic field in a pipe; and
a plurality of sensor blocks, each sensor block supporting at least one sensor for sensing said magnetic field;
wherein said sensor blocks are arranged adjacent to each other along a circumference direction of the body to form an array, the array extending around at least a part of the circumference of the body, each sensor block is movable in a radial direction relative to said body, and each sensor block in the array is shaped such that one axial edge of each sensor block circumferentially overlaps the opposite axial edge of an adjacent sensor block, at least when the sensor blocks are in a radially innermost position,
wherein that one axial end of each of said sensor blocks is circumferentially offset relative to the other axial end of the corresponding one of said sensor blocks, and
wherein an intermediate part of each of said sensor blocks is circumferentially offset relative to said one axial end in the opposite direction to the offset of said intermediate part relative to said other axial end.

2. An in-line pipe inspection tool according to claim 1, wherein each of said sensor blocks supports a plurality of sensors.

3. An in-line pipe inspection tool according to claim 1, further including a carrier, wherein the sensor blocks are connected to the carrier by a flexible linkage.

4. An in-line pipe inspection tool according to claim 1, wherein the sensor blocks are triangular, with alternating sensor blocks having their apexes pointing in opposite axial directions.

5. An in-line pipe inspection tool according to claim 1, wherein the sensor blocks are T shaped, with the left of the T of alternating sensor blocks pointing in opposite axial directions.

6. An in-line pipe inspection tool according to claim 1, further comprising:
a carrier extending along the circumference direction and on which each of the sensor blocks are mounted, wherein the carrier comprises a plurality of support parts connected by a deformable link, the sensor blocks being mounted on the support parts.

7. An in-line pipe inspection tool comprising:
a body;
magnets mounted in said body for generating a magnetic field in a pipe; and
a plurality of sensors for sensing said magnetic field;
wherein said sensors are mounted on sensor blocks, which sensor blocks are arranged adjacent to each other in an array, the array extending around at least a part of the circumference of the body, and the array includes a carrier on which the sensor blocks are mounted, the carrier having a circumferential length which is variable, thereby to vary the circumferential spacing between the sensor blocks.

8. An in-line pipe inspection tool according to claim 7, wherein said carrier comprises a plurality of support parts connected by a deformable link said sensor blocks being mounted on said support parts.

9. An in-line pipe inspection tool according to claim 7, wherein said body comprises a plurality of moveable parts, movement of said parts causing said varying of the circumferential length of said carrier.

10. An in-line pipe inspection tool according to claim 7, wherein each sensor block in the array is shaped such that one axial edge of each sensor block circumferentially overlaps the opposite axial edge of an adjacent sensor block, at least when the sensor blocks are in a radially innermost position.

11. An in-line pipe inspection tool according to claim 10, wherein that one axial end of each of said sensor blocks is circumferentially offset relative to the other axial end of the corresponding one of said sensor blocks.

12. An in-line pipe inspection tool according to claim 11, wherein an intermediate part of each of said sensor blocks is circumferentially offset relative to said one axial end in the opposite direction to the offset of said intermediate part relative to said other axial end.

13. An in-line pipe inspection tool according to claim 7, wherein the sensor blocks are triangular, with alternating sensor blocks having their apexes pointing in opposite axial directions.

14. An in-line pipe inspection tool according to claim 7, wherein the sensor blocks are T shaped, with the left of the T of alternating sensor blocks pointing in opposite axial directions.

15. An in-line pipe inspection tool comprising:
a body;
magnets mounted in said body for generating a magnetic field in a pipe;
a plurality of sensor blocks, each sensor block supporting at least one sensor for sensing said magnetic field; and
a carrier extending along the circumference direction and on which the sensor blocks are mounted, wherein the carrier comprises a plurality of support parts connected by a deformable link, the sensor blocks being mounted on the support parts,
wherein said sensor blocks are arranged adjacent to each other along a circumference direction of the body to form an array, the array extending around at least a part of the circumference of the body, each sensor block is movable in a radial direction relative to said body, and each sensor block in the array is shaped such that one axial edge of each sensor block circumferentially overlaps the opposite axial edge of an adjacent sensor block, at least when the sensor blocks are in a radially innermost position, and wherein said body comprises a plurality of moveable parts, movement of said parts causing a change of a circumferential length of the carrier.

16. An in-line pipe inspection tool comprising:
a body;
magnets mounted in said body for generating a magnetic field in a pipe;
a plurality of sensors for sensing said magnetic field; and
a plurality of sensor blocks configured to carry the plurality of sensors,
wherein a sensor block has a first end free and a second end, opposite to the first end, connected to a corresponding support attached to the body so that the sensor block is free to move away or towards the body depending whether a diameter of a pipe in which the in-line pipe is changing,
the sensor block having a face configured to face the pipe and carry more than one sensors, and
wherein the body comprises a plurality of moveable parts, movement of said parts causing a change in a circumferential length of a carrier configured to connect to the support.

17. An in-line inspection tool comprising:
a body;
magnets mounted in said body for generating a magnetic field in a pipe;
a plurality of sensors for sensing said magnetic field; and
a plurality of sensor blocks configured to carry the plurality of sensors,
wherein a sensor block has a first end free and a second end, opposite to the first end, connected to a corresponding support attached to the body so that the sensor block is free to move away or towards the body depending whether a diameter of a pipe in which the in-line pipe is changing,
the sensor block having a face configured to face the pipe and carry more than one sensors, and
wherein an axial end of each of said sensor blocks is circumferentially offset relative to another axial end of the corresponding one of said sensor blocks, and an intermediate part of each of said sensor blocks is circumferentially offset relative to said one axial end in the opposite direction to the offset of said intermediate part relative to said other axial end.

* * * * *